United States Patent [19]

Delbard

[11] Plant 4,330

[45] Nov. 7, 1978

[54] ROSE PLANT

[75] Inventor: Georges Delbard, Paris, France

[73] Assignee: Armstrong Nurseries, Inc., Ontario, Calif.

[21] Appl. No.: 855,959

[22] Filed: Nov. 30, 1977

[51] Int. Cl.[2] ..... A01H 5/00

[52] U.S. Cl. ..... Plt./22

[58] Field of Search ..... Plt./22

*Primary Examiner*—Robert E. Bagwill
*Assistant Examiner*—James R. Feyrer
*Attorney, Agent, or Firm*—Andrew R. Klein

[57] ABSTRACT

A somewhat tender seedling bush rose of the Floribunda class, for greenhouse and outdoor cultivation, both for cut flowers and for garden decoration, characterized primarily in that the coloration of its blooms is a rather unique shade of orange. The flowers are large, relatively speaking, in comparison with roses of the Floribunda class, and contain comparatively large numbers of petals and petaloids. The plant is a free to vigorous grower and its peduncles carry numerous stipitate glands and a few small prickles.

1 Drawing Figure

This invention relates to a new variety of Floribunda rose. The plant is a somewhat tender bush seedling, of free to vigorous growth. It is upright-spreading in form and much branched.

The seed parent, an unnamed, undisseminated seedling, was a Floribunda rose with small to medium-size flowers of coral pink coloration and 20 to 25 petals per bloom. The new variety is a Floribunda rose with relatively large flowers of distinct orange coloration and 25 to 36 petals plus 5 to 7 petaloids.

The pollen parent is likewise an unnamed, undisseminated seedling rose. It is not presently available for comparison. The ancestors of this seedling were: (Spartan x Mandrina).

Spartan generally bears somewhat smaller (3 to 3½-inch) flowers with somewhat fewer (about 30) petals than the new rose. Its color varies from orange-red to reddish-coral. The new rose has 3¼ to 4-inch flowers with 25 to 36 petals plus 5 to 7 petaloids, and its color is distinctly orange.

Mandrina produces 2½ to 3-inch, flat, orange-red flowers with about 30 petals; the new rose has large (3¼ to 4-inch)flowers, cupped to high-centered, with 25 to 36 petals plus 5 to 7 petaloids, and it is clearly orange in color.

The new cultivar holds its distinguishing characteristics through succeeding propagations by budding. It was first propagated in Evry Essonne, France, but the plant described herein was one derived from budwood of that propagation, and was grown in Ontario, Calif. References herein to the growth and behavior of the plant pertain to plants raised in Southern California.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

FLOWER

The new variety bears its flowers sometimes singly, but usually there are three or more, in irregular clusters, on normal, short to long stems. The plant blooms abundantly, both outdoors and in the greenhouse, and nearly continuously during the growing season. It has a slight tea to spicy fragrance.

BUD

The peduncle is average length to long, erect and stiff, with numerous stipitate glands and a few small prickles. The color is between Moderate Yellow Green, 5GY5/6, and Strong Yellow Green, 2.5GY6/8.

Before the calyx breaks, the bud is medium in size, medium-length, pointed and ovoid in form, with a conspicuous neck. There are foliaceous appendages on the surface of the bud, with slender foliaceous parts usually extending beyond the tip of the bud equal to one-fourth or more of its length.

As the calyx breaks, the color is between Strong Reddish Orange, 10R5/11, and Dark Reddish Orange, 7.5R4/11. The inner surface of the sepals carries a fine tomentum, the margins being lined with stipitate glands and/or hairs.

As the first petal opens, the bud is of average size, medium length, and pointed to urn-shaped in form. The color on the outside of the petal is between Strong Orange, 2.5YR6/12, and Strong Reddish Orange, 7.5R5/13, with a small area at the base near Vivid Greenish Yellow, 7.5Y8/12. The inside surface of the petal is more brilliant than a color between Strong Orange, 2.5YR6/12, and Strong Reddish Orange, 10R5/11, with a small area at the base near Vivid Yellow, 5Y8/12. The bud opens up well and is not retarded or prevented from opening by cold, hot, wet, or dry weather.

BLOOM

The size of the bloom when fully open is average to large, ranging from 3¼ to 4 inches, or 8 to 10 centimeters, in diameter. The petalage is double, with from 25 to 36 petals arranged regularly, plus 5 to 7 petaloids. The bloom is high centered at first, becoming cupped to high centered.

At first the petals remain tightly cupped, with tips reflexed outward, becoming later at maturity more loosely cupped, with tips reflexed outward. Sometimes the flowers are "quartered" or partially "quartered"; sometimes the petals are folded or arranged irregularly.

PETALS

The petals are thick and leathery, and are slightly velvety on the inside with the outside slightly shiny to satiny. The outside petals are nearly round, intermediate petals are broadly obovate and inside petals obovate. Their colors may be modified by being shaded and/or washed with other colors.

The paragraphs immediately following describe color values observed in a flower newly opened in the month of August. The plant had been grown in a greenhouse, in Ontario, Calif., but the color values are essentially the same for flowers grown outdoors.

The outer surface of the outside petal is between Strong Orange, 2.5YR7/10, and Strong Reddish Orange, 7.5R5/13, with a small area at the base near Brilliant Yellow, 5Y9/9. The inner surface of the outside petal is more brilliant than a color between Strong Orange, 2.5YR6/12, and Strong Reddish Orange, 10R5/11, with a small area at the base near Vivid Yellow, 2.5Y8/12.

The intermediate petals and the inner petals are the same in coloration. The outer surface of each is between Strong Orange, 5YR7/11, and Strong Reddish Orange, 10R6/12, with a small area at the base near Brilliant Yellow, 2.5Y9/9. The inner surface is between Strong Orange, 5YR7/11, and Strong Reddish Orange, 10R6/12, except more brilliant, with a basal area near Vivid Yellow, 2.5Y8/12.

The paragraph immediately following describes the color values observed in a bloom which had been open for 3 days, in a greenhouse, in the month of August. The plant had been grown in a greenhouse in Ontario, Calif. It may be observed that color values in flowers grown outdoors usually contain more yellow.

The outer surface of both the outside and inside petals was between Strong Orange, 5YR7/11, and Strong Reddish Orange, 7.5R6/12, with a small area at the base near Brilliant Greenish Yellow, 7.5Y9/8. The inner surface of both the outside and inside petals was more vivid than a color between Strong Orange, 5YR7/11, and Strong Reddish Orange, 7.5R6/12, with a small area at the base near Vivid Greenish Yellow, 7.5Y8/12.

The general color effect of the newly opened flower is more vivid than a color between Strong Orange, 7.5YR7/11, and Strong Reddish Orange, 10R5/11. The bloom, after being three days open, gives a general color effect ranging between Strong Orange, 5YR7/11, and Strong Reddish Orange, 10R6/12.

The petals persist, fading to a color between Pale Orange Yellow, 7.5YR9/4, and Light Orange, 2.5YR8/6. They are not particularly affected by cold, hot, wet or dry weather.

The flower on the bush in the garden persists for from 4 to 5 days in the month of August, in the locality named. Cut roses grown outdoors and kept at living-room temperatures will last from 3 to 5 days in the month of June. Cut roses grown in the greenhouse and kept at living-room temperatures will last from 4 to 5 days in the month of August.

REPRODUCTIVE ORGANS

The stamens are average in number, regularly arranged about the pistils, a few of them being tucked in the calyx.

The filaments are of medium length, and near Vivid Yellow, 2.5Y8/12, in color. Most are with anthers.

The anthers are small to medium in size, and all open approximately at once. The color of the margins just prior to release of pollen is between Moderate Orange Yellow, 10YR8/10, and Strong Orange Yellow, 7.5YR7/11. The color of the center, exterior part of the anther is near Brilliant Yellow, 2.5Y9/9.

Pollen is moderately abundant, and near Strong Orange Yellow, 7.5YR7/11, in color.

The pistils are approximately 115 in number, this being average.

The styles are uneven, of average length, thin caliper, and somewhat loosely bunched. They are between Strong Red, 5R4/12, and Dark Red, 2.5R3/7, in color, except near the base.

The stigma is near Pale Orange Yellow, 7.5YR9/4, in color.

Most of the ovaries are enclosed in the calyx, but some protrude therefrom.

The hips are of average length, globular in form but flat across the top. At half maturity, the color of the hips is near Strong Yellow Green, 5GY6/8, covered with a light bloom. They are moderately smooth, with moderately thick, fleshy walls. It will be noted that this plant does not set many hips naturally outdoors.

Sepals are still present when the hip is at half maturity, but brittle at the abscission layer near base of the sepal. They are medium-length, spear-shaped and recurved. On the inside, their coloration is light greenish gray. On the outside, the coloration is between Strong Yellow Green, 2.5GY6/8, and Moderate Yellow Green, 2.5GY5/5.

There are many small seeds, from 20 to 25 in number.

PLANT

Foliage

The compound leaves usually comprise 3 to 5 leaflets. These are normal in quantity, medium in size, moderately heavy to somewhat leathery, glossy and slightly wavy. The leaflets are ovate in shape, with apex acute, base obtuse, and margin simply serrate.

The mature foliage displays upon its upper surface a color which is between Moderate Olive Green, 5GY4/3, and Grayish Olive Green, 5GY3/2. The under surface is near Moderate Yellow Green, 5GY5/6, highly overlaid with light gray bloom.

The young foliage on its upper surface is between Dark Red, 2.5R3/7, and Dark Red, 5R3/7; on its under surface it is near Dark Red, 2.5R3/7.

The rachis is average in size, grooved on the upper side, with some stipitate glands on the edges. The under side is sparsely prickly.

The stipules are medium-length, medium-width, and with medium-length points turning out at an angle of more than 45°, sometimes slightly recurved toward the stem.

The plant displays an average resistance to mildew, when compared with other varieties now in commerce under comparable conditions, when grown at Ontario, Calif.

Growth

The plant is of upright-spreading habit, bushy and much branched. It displays a free to vigorous growth. Its canes are of medium caliper.

The main stems are between Moderate Reddish Brown, 2.5YR3/3, and Dark Red, 5R3/7, in color, with lenticels and older bark becoming corky. They carry from few to several large prickles, which are medium-length, almost straight to hooked slightly downward, with medium-length moderately broad base. There are few small prickles, and the coloration of both large and small prickles is Moderate Brown, 7.5YR4/5, aging to gray. There are no hairs.

The branches are near Moderate Yellow Green, 2.5GY5/5, in color, sometimes slightly overlaid with near Dark Red, 2.5R3/7. They carry from few to several large prickles, which are sharp, of medium length, and hooked slightly downward, with moderately long, moderately broad base. These large prickles, as well as the few small prickles, are near Strong Yellowish Brown, 10YR5/6, in color. There are no hairs.

New shoots are near Strong Yellow Green, 7.5GY6/8, in color, moderately to heavily overlaid with near Dark Red, 2.5R3/7. They carry a few large prickles, which are medium-length, hooked slightly downward, with medium-length narrow base. There are very few small prickles, and both large and small prickles are the same coloration as the new shoots. There are no hairs.

I claim:

1. The new and distinct variety of Floribunda rose plant substantially as described and illustrated herein, said plant being of free to vigorous growth habit, and having numerous stipitate glands and a few small prickles on its peduncles, the flowers of said plant being characterized in that they are from about 3½ to about 4 inches in diameter, and comprise from 25 to 36 petals with 5 to 7 petaloids, and have an overall coloration which is substantially entirely expressed in shades of orange.

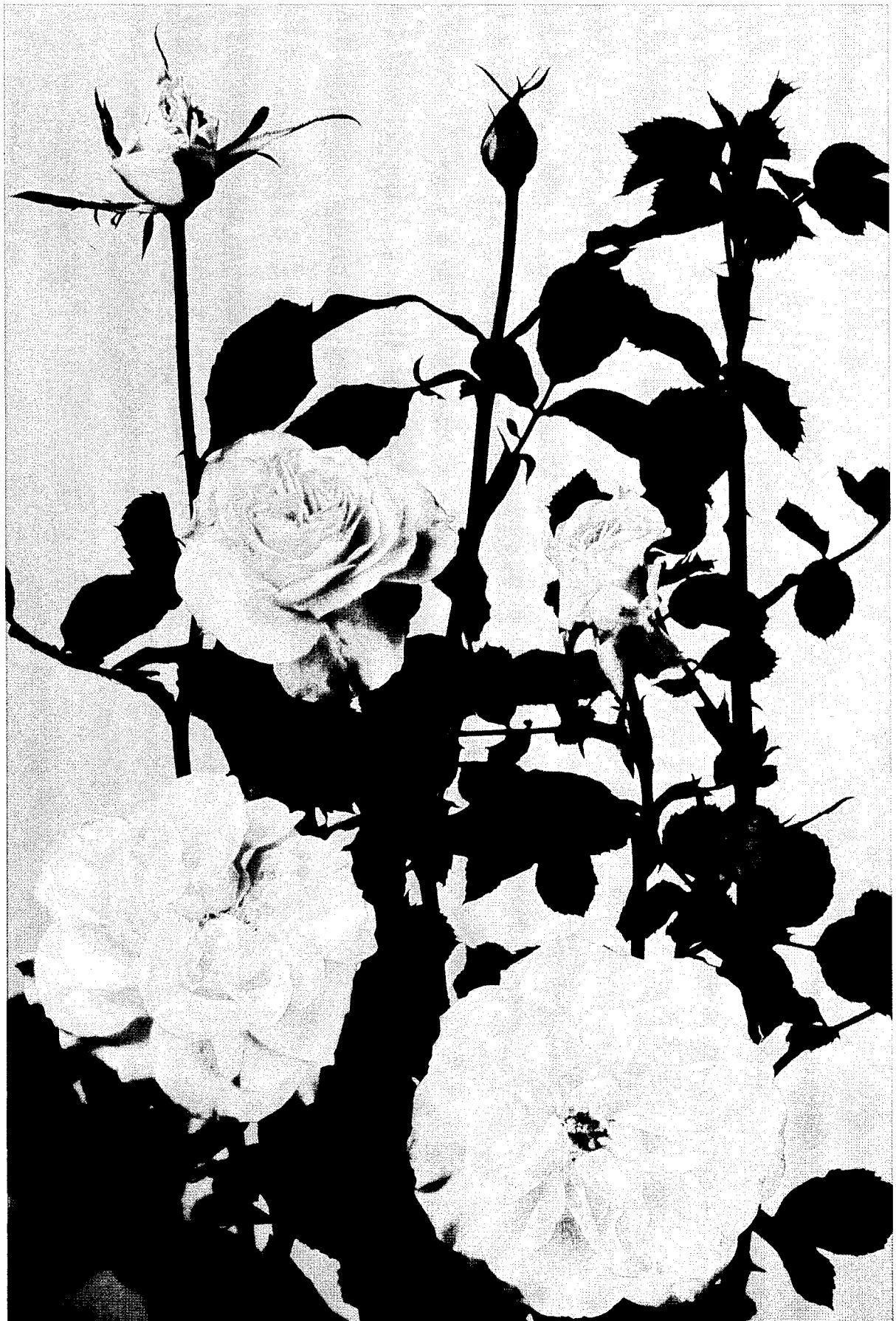

* * * * *